United States Patent
Liu et al.

(10) Patent No.: US 12,228,488 B2
(45) Date of Patent: Feb. 18, 2025

(54) DEVICE AND METHOD FOR MEASURING MICRO/NANO-SIZED PARTICLES

(71) Applicant: RESUN (SHENZHEN) TECH CO., LTD., Shenzhen (CN)

(72) Inventors: Ke Liu, Shenzhen (CN); Gui Xiong, Shenzhen (CN); Zhe Wang, Shenzhen (CN)

(73) Assignee: Resun (Shenzhen) Tech Co., Ltd., Shenzhen (CN)

( * ) Notice: Subject to any disclaimer, the term of this patent is extended or adjusted under 35 U.S.C. 154(b) by 375 days.

(21) Appl. No.: 17/757,888

(22) PCT Filed: Nov. 12, 2020

(86) PCT No.: PCT/CN2020/128400
§ 371 (c)(1),
(2) Date: Jun. 23, 2022

(87) PCT Pub. No.: WO2021/098583
PCT Pub. Date: May 27, 2021

(65) Prior Publication Data
US 2023/0236104 A1    Jul. 27, 2023

(30) Foreign Application Priority Data
Nov. 22, 2019 (CN) .......................... 201911158297.3

(51) Int. Cl.
*G01N 15/02* (2024.01)
*G01N 15/00* (2024.01)

(52) U.S. Cl.
CPC . *G01N 15/0266* (2013.01); *G01N 2015/0038* (2013.01); *G01N 2015/0294* (2013.01)

(58) Field of Classification Search
CPC ....... G01N 15/0266; G01N 2015/0038; G01N 2015/0294; G01N 15/00
See application file for complete search history.

(56) References Cited

U.S. PATENT DOCUMENTS 10,458,893 B2 * 10/2019 Chiang .............. G01N 15/0606
10,670,514 B2 *  6/2020 Liu ..................... G01N 15/1459
(Continued)

FOREIGN PATENT DOCUMENTS

CN    101382482 A    3/2009
CN    101548338 A    9/2009
(Continued)

OTHER PUBLICATIONS

Official Action mailed to the Corresponding Chinese Patent Application No. 201911158297 dated Jul. 19, 2024.
(Continued)

*Primary Examiner* — Octavia Hollington
(74) *Attorney, Agent, or Firm* — Rosenberg, Klein & Lee

(57) ABSTRACT

The device (100) comprises a cavity (101) and at least two microporous membranes (102), wherein the microporous membranes (102) are arranged in series in the cavity (101) and divide the cavity (101) into a plurality of chambers (1011); each of the microporous membranes (102) is provided with micropores (103), and two adjacent chambers (1011) are in communication via the micropores (103); and each of the chambers (1011) is provided with an electrode (1012).

7 Claims, 4 Drawing Sheets

(56) References Cited

U.S. PATENT DOCUMENTS

| | | | | |
|---|---|---|---|---|
| 2007/0292750 A1* | 12/2007 | Beard | ............... | H01M 4/043 |
| | | | | 429/217 |
| 2011/0120890 A1 | 5/2011 | MacPherson et al. | | |
| 2014/0099726 A1* | 4/2014 | Heller | .............. | G01N 33/48721 |
| | | | | 422/82.01 |
| 2018/0372713 A1* | 12/2018 | Stamm | ............. | G01N 27/44791 |
| 2022/0404348 A1* | 12/2022 | Liu | ................. | G01N 33/48721 |

FOREIGN PATENT DOCUMENTS

| | | | | | |
|---|---|---|---|---|---|
| CN | 102271922 A | * | 12/2011 | ......... | B05B 17/0638 |
| CN | 202522535 U | * | 11/2012 | | |
| CN | 103874914 A | | 6/2014 | | |
| CN | 104568684 A | | 4/2015 | | |
| CN | 105247341 A | | 1/2016 | | |
| CN | 106796169 A | | 5/2017 | | |
| CN | 109580718 A | | 4/2019 | | |
| CN | 109612890 A | * | 4/2019 | ......... | G01N 15/0266 |
| CN | 110823773 A | | 2/2020 | | |
| CN | 211122430 U | | 7/2020 | | |
| EP | 1645628 A1 | | 4/2006 | | |
| JP | J006258540 A | | 9/2006 | | |
| JP | 2012230080 A | | 11/2012 | | |
| KR | 20060091021 A | * | 8/2006 | | |

OTHER PUBLICATIONS

European Search Report mailed to Corresponding Patent Application No. 20890268.4-1001 dated Jan. 3, 2023.

* cited by examiner

DEVICE AND METHOD FOR MEASURING MICRO/NANO-SIZED PARTICLES

CROSS-REFERENCE TO RELATED APPLICATIONS

This application is a 371 of International Application No.PCT/CN2020/128400, filed Nov. 12, 2020, which claims the priority of Chinese Patent Application No. 201911158297.3 filed on Nov. 22, 2019, the entire contents of which are hereby incorporated by reference.

TECHNICAL FIELD

The present application relates to the technical field of micro/nano-sized particle measurement, and in particular, to a device and method for measuring micro/nano-sized particles.

BACKGROUND

Based on the special attributes of particulate matter, particulate matter is widely used in medicine, chemical industry, materials and other fields. In the application of particulate matter, it is very important to measure the three-dimensional shape and other attributes of particulate matter (hereinafter referred to as particles).

The inventors realized that a particle measurement equipment currently used commonly includes optical microscopes, scanning electron microscopes and transmission electron microscopes, but due to the low resolution of optical microscopes, it is difficult to observe particles with a size less than 300 nanometers by optical microscopes, which is not suitable for micro/nano-sized particle measurement. Scanning electron microscopy and transmission electron microscopy can obtain the three-dimensional morphology of particles by tilting the particle samples at different angles under vacuum conditions, but cannot obtain real morphological information for particle samples that need to be measured in solution state or biological particle samples. Therefore, there is still a problem in tradition that the three-dimensional morphology of micro/nano-sized particles in solution cannot be measured.

SUMMARY

There are provided a device for measuring micro/nano-sized particles, and a method for measuring micro/nano-sized particles according to embodiments of the present disclosure.

The Technical Solution is as Below:

In one aspect, a device for measuring micro/nano-sized particles, comprising a cavity and at least two microporous membranes. The microporous membranes are arranged in series in the cavity and divide the cavity into a plurality of chambers. Each of the microporous membranes is provided with micropores, and two adjacent chambers are in communication via the micropores. Each of the chambers is provided with an electrode.

In another aspect, a method for measuring micro/nano-sized particles, comprising: allowing the micro/nano-sized particles to be measured to continuously pass through the micropores of the aforementioned device along with an electrolyte solution; acquiring electric signal data between two electrodes adjacent to each of the micropores in the process of the micro/nano-sized particles passing through each of the micropores; and determining attribute data of the micro/nano-sized particles according to the electric signal data.

In the above technical solution, the cavity of the device for measuring micro/nano-sized particles is divided into a plurality of chambers by a series of microporous membranes, and two adjacent chambers are communicated through the micropores on the microporous membrane, and each chamber has electrodes. In the measurement state, each chamber is filled with an electrolyte solution, and the electrolyte solution contains the micro/nano-sized particles to be measured. The micro/nano-sized particles pass through each micropore in turn with the flow of the electrolyte solution. By analyzing the electrical signal data between two electrodes adjacent to the micropore, the three-dimensional morphological attributes of the micro/nano-sized particles to be measured in the electrolyte solution can be obtained, thereby realizing the measurement of the three-dimensional morphological attributes of the micro/nano-sized particles in the solution state.

It is to be understood that both the foregoing general description and the following detailed description are exemplary and explanatory only and are not restrictive of the application.

BRIEF DESCRIPTION OF THE DRAWINGS

The accompanying drawings, which are incorporated in and constitute a part of this specification, illustrate embodiments consistent with the application and together with the description serve to explain the principles of the application.

Figure 1:
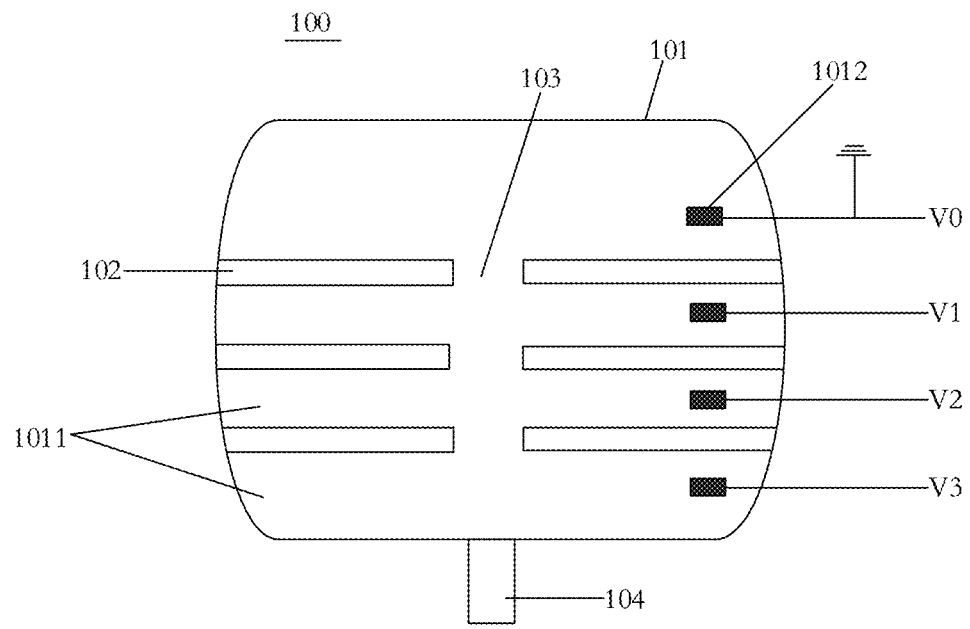
FIG. 1 is a cross-sectional view of a device for measuring micro/nano-sized particles according to an exemplary embodiment.

Numeral description: 100, device for measuring micro/nano-sized particles; 101, cavity; 1011, chamber; 1012, electrode; 102, microporous membrane; 103, micropore; 104, liquid driving device; 105, electrolyte solution; 106, micro/nano-sized particles.

By the above-mentioned drawings, the specific embodiments of the present application have been shown, and a more detailed description will follow. These drawings and written descriptions are not intended to limit the scope of the concepts of the present application in any way, but by reference to specific embodiments, the concepts of the present application are explained to those skilled in the art.

DETAILED DESCRIPTION

The description will now be made in detail of exemplary embodiments, examples of which are illustrated in the accompanying drawings. Where the following description refers to the drawings, the same numerals in different drawings refer to the same or similar elements unless otherwise indicated. The implementations described in the illustrative examples below are not intended to represent all implementations consistent with this application. Rather, they are merely examples of apparatus and methods consistent with some aspects of the present application as recited in the appended claims.

First of all, it should be noted that the micro/nano-sized particles described in this embodiment refer to particle physics with a size in the micro-and nano-scale, usually including organic particles, inorganic particles, magnetic particles, silica particles, agarose gel particles, styrene particles, metal particles, colloidal particles, particles conjugated with molecules, particles conjugated with biomolecules, particles conjugated with immunoglobulins, particles conjugated with nucleic acids, biological particles, biological cells, blood cells, sperm, egg cells, microbial cells, bacterial cells, fungal cells, viruses, subcellular organelles, mitochondria, nuclei, chloroplasts, lysosomes, ribosomes, atomic particles, ionic particles, molecular particles, polymeric particles, nucleic acids and their chemical variants, deoxyribonucleic acid and chemical variants thereof, nucleic acids and chemical variants thereof, proteins and chemical variants thereof. Among them, the inorganic particles usually include particulate matter such as silicon dioxide, titanium dioxide, aluminum oxide, calcium carbonate, and aluminum nitride.

Micro/nano-sized particles have unique electrical, optical and magnetic attributes. Physical attributes such as particle size and potential of micro/nano-sized particles have a great influence on their performance. Therefore, it is necessary to measure the physical attributes of micro/nano-sized particles. For example, a biological macromolecule includes four types of substances such as nucleic acids, proteins, carbohydrates and lipids. These biological macromolecules exist in the form of micro/nano-sized particles in the living body. By measuring the physical attributes of these biological macromolecules, the study of life behavior will be of great significance.

Referring to FIG. 1, FIG. 1 is a cross-sectional view of a device for measuring micro/nano-sized particles according to an exemplary embodiment. The device can be used to measure three-dimensional morphological attributes of micro/nano-sized particles such as the electrical mobility, sphericity value, and particle size and other.

As shown in FIG. 1, in an exemplary embodiment, the device 100 for measuring micro/nano-sized particles includes a cavity 101 and at least two microporous membranes 102 (three are shown in FIG. 1). Each microporous membrane 102 is arranged in series in the cavity 101, dividing the cavity 101 into a plurality of chambers 1011, and the microporous membrane 102 is provided with micropores 103, so that two adjacent chambers 1011 are connected through the micropores 103, and each chamber 1011 has electrodes 1012 therein.

Figure 2:
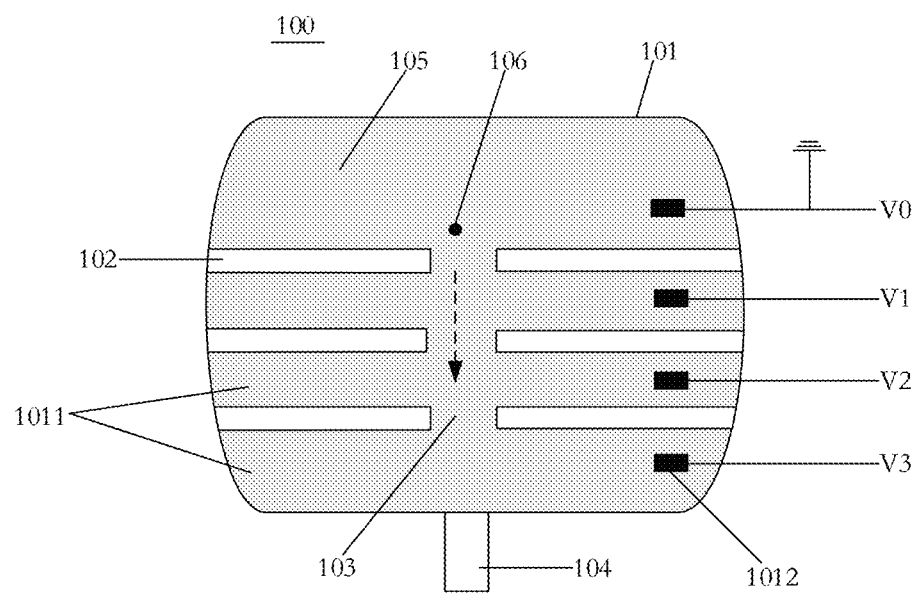
FIG. 2 is a schematic diagram of the device for measuring micro/nano-sized particles shown in FIG. 1 in a measurement state.

In the measurement state, as shown in FIG. 2, each chamber 1011 of the device 100 is filled with an electrolyte solution 105, and the electrolyte solution 105 contains the micro/nano-sized particles 106 to be measured, so as to provide a solution environment for the measurement of the micro/nano-sized particles 106. The micro/nano-sized particles 106 pass through each micropore 103 in turn with the flow of the electrolyte solution 105, and the electrode 1012 at one end of the cavity 101 is grounded, and the other electrodes 1012 are respectively loaded with voltages of different magnitudes. Exemplarily, the conductivity of the electrolyte in the electrolyte solution 105 may be in the range of $10^{-6}$ to $10^{-3}$ S/cm (Siemens per meter).

The electrolyte solution 105 flows from the chamber 1011 at one end of the chamber 101 to the chamber 1011 at the other end of the chamber 101, and its flow direction is determined by the driving direction of the liquid driver 104 at one end of the chamber 101. As shown in FIGS. 1 and 2, in one embodiment, the liquid driver 104 is located at the bottom end of the cavity 101 and is adjacent to the cavity 1011 at the bottom end. The driving direction of the liquid driver 104 for the electrolyte solution 105 can be driven from the chamber 1011 at the top to the chamber 1011 at the bottom as shown in FIG. 2, or from the chamber 1011 at the bottom to the chamber 1011 at the top, which is not limited here. The liquid driver 104 may also be located at the top end of the cavity 101 and adjacent to the cavity 1011 at the top end.

The driving mode of the liquid driver 104 can be electric field force driving, hydraulic driving, magnetic field driving, fluid driving, air pressure driving, osmotic pressure driving, Brownian motion driving, capillary force driving, temperature difference diffusion driving, etc. Correspondingly, the liquid driver 104 may be a device that can provide a driving force for the flow of the electrolyte solution 105, such as a liquid pump, a pneumatic device, a syringe, and the like. Exemplarily, the driving mode of the liquid driver 104 adopts any one of electric field driving, hydraulic driving, and magnetic field driving, so as to provide a fixed driving force for the flow of the electrolyte solution 105, thereby driving the electrolyte solution 105 to flow stably.

In addition, the electrode 1012 at one end of the cavity 101 is grounded, and voltages of different magnitudes are applied to the remaining electrodes 1012, and the order of the applied voltages corresponds to the distance between the electrode 1012 and the grounded electrode 1012. As shown in FIG. 1, if the electrode 1012 in the top chamber 1011 is grounded, that is, V0=0V, the magnitude of the applied voltage on the other three electrodes 1012 is V3≥V2≥V1, so that the strength of the electric field formed between the two adjacent electrodes 1012 increases sequentially, ensuring that the micro/nano-sized particles 106 continuously pass through each micropore 103 along with the flow of the electrolyte solution 105. The electrode 1012 can be made of platinum or silver chloride and other materials.

During the process that the micro/nano-sized particles 106 pass through each micropore 103 in turn with the flow of the electrolyte solution 105, the electrical signal data between the two electrodes 1012 adjacent to the micropore 103 are obtained by respectively measured when the micro/nano-sized particles 106 pass through the micropore 103. By analyzing the obtained electrical signal data, three-dimensional morphological attributes such as electrical mobility, sphericity value, particle size, of the micro/nano-sized particles 106 can be obtained, thereby solving the problem that the attributes of the micro/nano-sized particles in solution state cannot be measured in tradition.

The microporous membrane 102 may be an organic membrane or an inorganic membrane.

In one embodiment, the microporous membrane 102 is an inorganic membrane, that is, the microporous membrane 102 is made of an inorganic material. Compared with an organic membrane, the inorganic membrane has better stretchability, which is beneficial for the micro/nano-sized particles 106 to flow with the electrolyte solution 105 and move through the micropores 103. Exemplarily, the microporous membrane 102 may be made of inorganic materials such as low-stress silicon nitride, silicon nitride or silicon wafers. The microporous membrane 102 made of these inorganic materials has better membrane-forming effect, and the manufacturing technology is also more mature.

The thickness of the microporous membrane 102 may be 1 nanometer to 10 micrometers, and the inner diameter of the micropores 103 may be 1 nanometer to 10 micrometers. The inner diameter of the micropore 103 is the diameter of the micropore 103, which refers to the distance in the direction perpendicular to the direction in which the micro/nano-sized particles 106 move through the device 100 during the measurement process. The micropore 103 can be cylindrical, rectangular parallelepiped, conical table, trapezoidal table and other geometric shapes. Exemplarily, when the micropore 103 is cylindrical, the inner diameter of the micropore 103 is the diameter of the bottom circle of the cylinder.

There is a separation distance between two adjacent microporous membranes 102, and the separation distance between two adjacent microporous membranes 102 may be the same or different. Exemplarily, the separation distance between two adjacent microporous membranes 102 may be 1 nanometer to 100 micrometers.

The microporous membrane 102 and the cavity 101 can be integrally formed, so that the shape of the device 100 has high stability. The microporous membranes 102 can also be arranged in the cavity 101 in a manner of membrane stacking, and there is a certain distance between each microporous membrane 102. For example, a plurality of fluid grooves can be arranged on the inner surface of the cavity 101, there is a certain distance between adjacent fluid grooves, and the microporous membrane 102 is fixed in the fluid groove, so as to realize the membrane stacking arrangement of the microporous membrane 102.

The positions, inner diameters and thicknesses of the micropores 103 on each microporous membrane 102 can be completely consistent, so that the centers of the micropores 103 are located on the same straight line, and the moving paths of the micro/nano-sized particles in the device 100 remain straight. The separation distance between two adjacent microporous membranes 102 may be the same or different.

In the above technical solution, the cavity of the device for measuring micro/nano-sized particles is divided into a plurality of chambers by a series of microporous membranes, and two adjacent chambers are communicated through the micropores on the microporous membrane, and each chamber has electrodes. In the measurement state, each chamber is filled with an electrolyte solution, and the electrolyte solution contains the micro/nano-sized particles to be measured. The micro/nano-sized particles pass through each micropore in turn with the flow of the electrolyte solution. By analyzing the electrical signal data between two electrodes adjacent to the micropore, the three-dimensional morphological attributes of the micro/nano-sized particles to be measured in the electrolyte solution can be obtained, thereby realizing the measurement of the three-dimensional morphological attributes of the micro/nano-sized particles in the solution state.

Another exemplary embodiment of the present invention also provides a method for measuring micro/nano-sized particles, which is implemented based on the device for measuring micro/nano-sized particles described in the above embodiments, so as to determine the micro/nano-sized particles to be measured attribute data. Exemplarily, the device for measuring micro/nano-sized particles described in the above embodiments is further configured with computer components such as a processor and a memory, and the method for measuring micro/nano-sized particles provided in this embodiment is executed by the computer components, so as to determine the attribute data of micro/nano-sized particles. Alternatively, the device for measuring micro/nano-sized particles described in the above embodiments is connected to an external computer equipment, so that the external computer equipment performs measurement according to the device for measuring micro/nano-sized particles described in the above embodiments to obtain measurement data, to execute the method for measuring micro/nano-sized particles provided in this embodiment, which is not limited here.

In the method for measuring micro/nano-sized particles provided in this embodiment, first enabling the micro/nano-sized particles to be measured so as to continuously pass through the plurality of micropores of the aforementioned device along with an electrolyte solution, and then acquiring electric signal data between two electrodes adjacent to each of the micropores in the process of the micro/nano-sized particles passing through each of the micropores, to determine attribute data of the micro/nano-sized particles according to the electric signal data.

It should be noted that a set of continuous electrical signal data can be obtained by collecting the corresponding electrical signal data during the continuous passage of the micro/nano-sized particles through a plurality of micropores. Based on the analysis of the continuous electrical signal data, attribute information related to the three-dimensional morphology of the micro/nano-sized particles can be determined.

The method provided in this embodiment will be described in detail below by taking the device 100 for measuring micro/nano-sized particles shown in FIG. 1 and FIG. 2 as an example.

In the device 100 shown in FIG. 1 and FIG. 2, three microporous membranes 102 are arranged in the cavity 101, and the microporous membranes 102 divide the cavity 101 into four chambers 1011. The micro/nano-sized particles 106 to be measured continuously pass through the three micropores 103 along with the flow of the electrolyte solution 105. In the process of flowing with the electrolyte solution 105, the micro/nano-sized particles 106 are prone to inversion, inclination, etc., so that the micro/nano-sized particles 106 pass through each micropore 103 in different postures. When the micro/nano-sized particles 106 pass through each micropore 103 in different postures, the electrical signal data between the two electrodes 1012 adjacent to the micropore 103 may be different.

Figure 3:
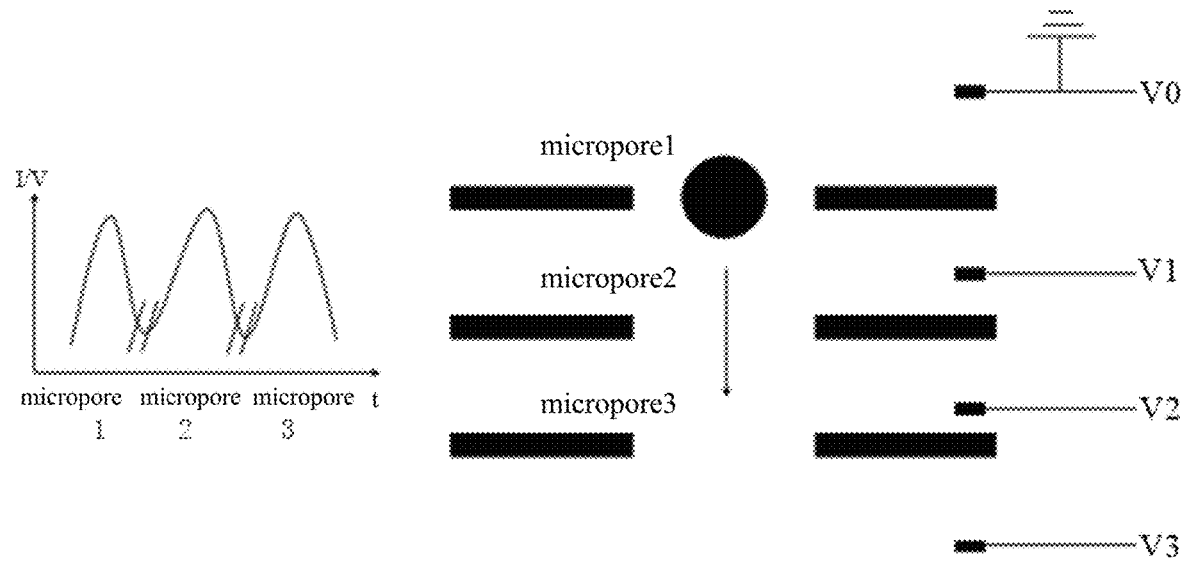
FIG. 3 is a schematic diagram of a set of continuous electrical signal data obtained by collecting electrical signal data between two electrodes adjacent to each micropore during process of a standard spherical particle continuously passing through each micropore of the device shown in FIG. 1.
Figure 4:
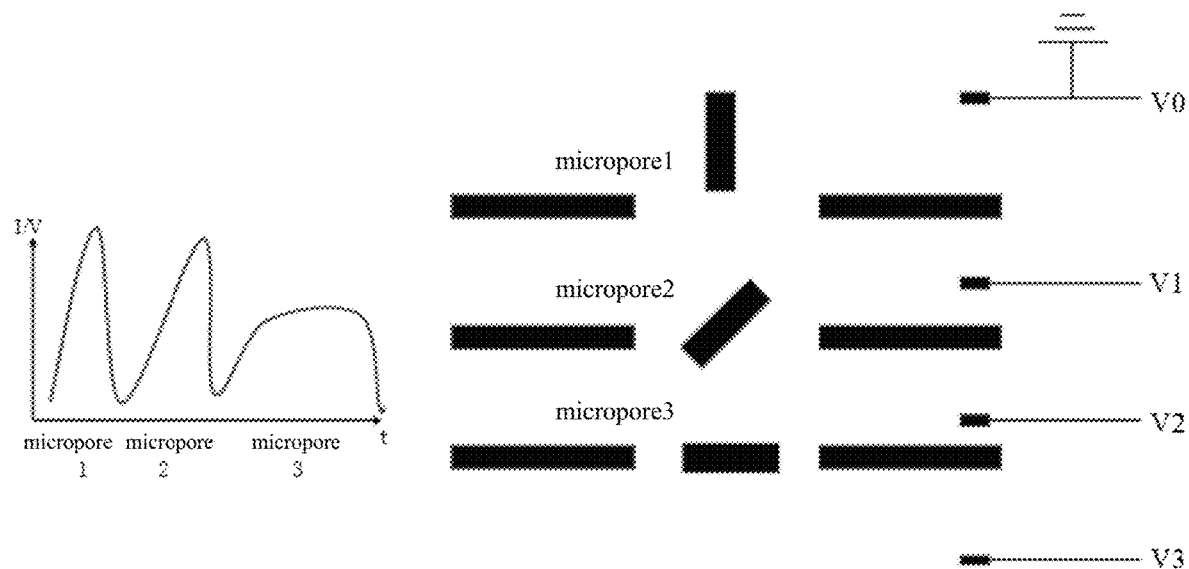
FIG. 4 is a schematic diagram of a set of continuous electrical signal data obtained by collecting electrical signal data between two electrodes adjacent to each micropore during process of a standard cube particle continuously passing through each micropore of the device shown in FIG. 1.

Referring to FIG. 3 and FIG. 4, FIG. 3 is a schematic diagram of a set of continuous electrical signal data obtained by collecting electrical signal data between two electrodes 1012 adjacent to each micropore 103 during the continuous passage of a standard spherical particle through each micropore 103, FIG. 4 is a schematic diagram of a set of continuous electrical signal data obtained by collecting electrical signal data between two electrodes 1012 adjacent to each micropore 103 during the continuous passage of a standard cube particle through each micropore 103.

It can be seen that for the micro/nano-sized particles 106 with uniform three-dimensional morphology, such as the spherical particles shown in FIG. 3, during the process of passing through each micropore 103, the electrical signals on the two electrodes 1012 adjacent to each micropore 103 have little difference. However, for the micro/nano-sized particles 106 with non-uniform three-dimensional morphology, such as the cuboid particles shown in FIG. 4, during the process of passing through each micropore 103, the electrical signals on the two electrodes 1012 adjacent to each micropore 103 is quite different.

In an exemplary embodiment, the attribute data of the micro/nano-sized particles 106 includes an electrical mobility of the micro/nano-sized particles 106. The speed of the micro/nano-sized particles 106 passing through two adjacent micropores 103 and the potential difference between the two adjacent micropores 103 can be determined according to the electrical signal data, so as to determine the electric mobility of the micro/nano-sized particles 106 when the micro/nano-sized 106 continuously pass through two adjacent micropores 103 according to the obtained speed and potential difference.

The time for the micro/nano-sized particles 106 continuously passing through two adjacent micropores 103 can be obtained according to the electrical signal data, and then the ratio of the distance between the two adjacent micropores 103 to the time can be calculated to determine the speed of the micro/nano-sized particles 106 continuously passing through two adjacent micropores 103. The potential difference between two adjacent micropores 103 can be determined according to the electric field strength and distance between two adjacent micropores 103.

Exemplarily, if the distance between two adjacent micropores 103 is 1000 nanometers, the time interval for the micro/nano-sized particles 106 passing through the two micropores 103 is 1 millisecond, and the resulting potential difference is 100 millivolts, then the calculated electric mobility of the micro/nano-sized particles 106 passing through the two adjacent micropores 103 is $10^{-8}$ $m^2v^{-1}s^{-1}$.

The surface potential of the micro/nano-sized particles 106 can be further determined according to the determined electric mobility of the micro/nano-sized particles 106 when passing through two adjacent micropores 103 continuously, and the surface potential of the micro/nano-sized particles 106 corresponds to the posture when the micro/nano-sized particles 106 passing through the micropores 103.

Therefore, according to the change of the surface potential of the micro/nano-sized particles 106 in the process of continuously passing through the two adjacent micropores 103, the posture change of the micro/nano-sized particles 106 in the process of continuously passing through the micropores 103 can be determined, so that three-dimensional morphology of the micro/nano-sized particles 106 can be obtained by analysis.

In another exemplary embodiment, the attribute data of the micro/nano-sized particles 106 includes a sphericity value of the micro/nano-sized particles 106. By dividing the electrical signal data into several signal units, and then comparing the signal units with the corresponding signal units of the standard signal, the contrast coefficient between the electrical signal data and the standard signal is obtained, so as to obtain the sphericity value of the standard signal with the highest contrast coefficient as the sphericity value of the micro/nano-sized particles 106.

Figure 5:
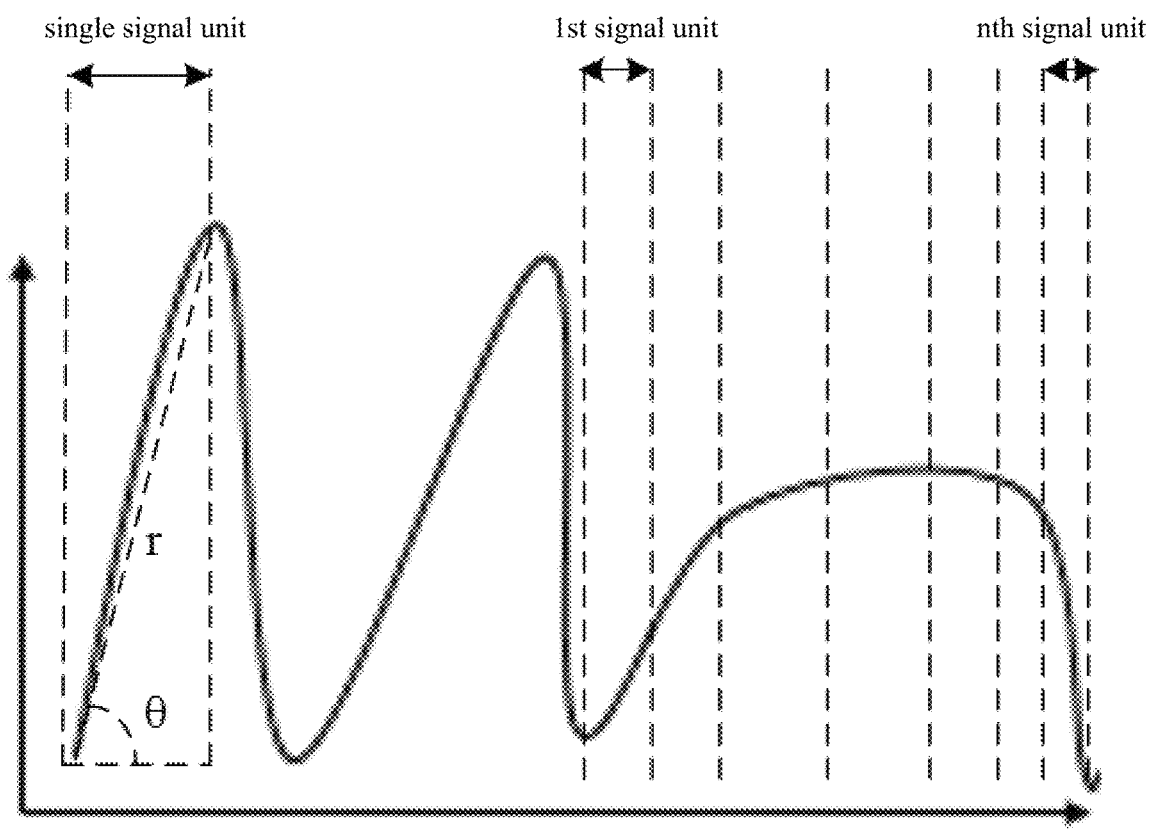
FIG. 5 is a schematic diagram illustrating signal unit dividing for electrical signal data according to an exemplary embodiment.

First of all, it should be noted that FIG. 5 is a schematic diagram of a set of electrical signal data collected in the process of a micro/nano-sized particle 106 passing through three micropores 103 continuously, which contains three independent electrical signal data, each independent electrical signal data respectively corresponds to the process of the micro/nano-sized particles 106 passing through different micropores 103, and the three independent electrical signal data are continuous in terms of time.

As shown in FIG. 5, for the electrical signal data with sinusoidal distribution, the electrical signal data can be divided by taking the electrical signal peak value as a dividing point, thereby obtaining two signal units. For the electrical signal data distributed in other forms, the electrical signal data can be divided according to the set time interval, or the electrical signal data can be divided according to the gradient change trend of the electrical signal, which is not limited here.

The electrical signal data is divided into several signal units, and the gradient function f(θ, r) of each signal unit needs to be calculated. The calculation formula of the gradient function f(θ, r) is as follows:

$$f(\theta, r) = \arctan(\theta)$$

Where r represents the slope length of a single signal unit, and θ represents the slope angle of a single signal unit.

The standard signal is known information obtained in advance, and is the electrical signal data collected during the movement of the micro/nano-sized particles 106 with determined sphericity values through the micropores 103. Therefore, the standard signal reflects the sphericity value of the micro/nano-sized particles 106. The standard signal needs to be divided into several signal units in advance according to the above method.

By comparing the slope function of each signal unit with the slope function of the corresponding signal unit of the standard signal, the contrast coefficient between each signal unit of the electrical signal data and each signal unit of the standard signal can be obtained, and the contrast coefficient reflects similarity between each signal unit. Therefore, the higher the contrast coefficient between the signal units, the closer the sphericity values between the micro/nano-sized particles 106 are.

For each electrical signal data, by calculating the average value of the contrast coefficients of all the signal units divided into which the electrical signal data is divided, the contrast coefficient between the electrical signal data and the standard signal is obtained.

In order to ensure the practicability of this embodiment, it is necessary to provide a variety of standard signals of the micro/nano-sized particles 106 with determined sphericity values in advance, and calculate the contrast coefficients between the electrical signal data obtained during the measurement process and different standard signals, to determine the sphericity value corresponding to the standard signal with the highest contrast coefficient as the sphericity value of the micro/nano-sized particles 106 to be measured.

Figure 6:
FIG. 6 is a schematic diagram of electrical signal data collected during the process of a 200 nm diameter styrene microsphere continuously passing through a plurality of micropores.

FIG. 6 is a schematic diagram of a set of electrical signal data collected during the process of a 200 nm diameter styrene microsphere continuously passing through three micropores 103 under an actual measurement environment. By analyzing the electrical signal data shown in FIG. 6 based on the above acquisition process of sphericity value, it can be obtained that the sphericity value of the styrene microsphere is 0.95.

It should be noted that, in general, for the nearly spherical micro/nano-sized particles 106, the sphericity value obtained by the method provided in this embodiment is above 0.8, while for the rod-shaped micro/nano-sized particles 106, the obtained sphericity value is 0.2 or less.

It should also be noted that there is also a certain correspondence between the aspect ratio of the micro/nano-sized particles 106 and the sphericity value of the micro/nano-sized particles 106. Therefore, the aspect ratio of the micro/nano-sized particles 106 also has a certain influence on the measurement of the sphericity value of the micro/nano-sized particles 106.

In another exemplary embodiment, the electrical signal data obtained during the measurement process can also be input into a machine learning model, so that the machine learning model can predict the three-dimensional shape of the micro/nano-sized particles 106 according to the input electrical signal data, so as to directly obtain the three-dimensional morphology of the micro/nano-sized particles.

It should be noted that the machine learning model used in this embodiment is pre-trained according to the electrical signal data between the two electrodes adjacent to the micropore 103 when the micro/nano-sized particles 106 with asymmetric morphology pass through the micropore 103.

In another exemplary embodiment, the attribute data of the micro/nano-sized particles 106 further includes a particle size of the micro/nano-sized particles 106. The initial particle size of the micro/nano-sized particles 106 is calculated according to the electrical conductivity of the electrolyte solution 105, the approximate spherical radius of the micro/nano-sized particles 106 and the radius of the micro/nano-sized particles 103. If the ratio of the approximate spherical radius of the micro/nano-sized particles 106 to the radius of the micro/nano-sized particles 103 is greater than the preset threshold, the correction coefficient is determined according to the ratio, and the initial particle size is corrected by the correction coefficient to obtain the particle size of the micro/nano-sized particles 106.

The calculation formula of the initial particle size VR of the micro/nano-sized particles 106 is as follows:

$$VR = (4\rho d^3)/(\pi D^4)$$

Wherein d represents the approximate spherical radius of the micro/nano-sized particles 106, D represents the radius of the micropore 103, and $\rho$ represents the conductivity of the electrolyte solution 105. If the particle size of the micro/nano-sized particles 106 is much smaller than the radius of the micro/nano-sized particles 103, for example, the ratio d/D of the approximate spherical radius of the micro/nano-sized particles 106 to the radius of the micro/nano-sized particles 103 is smaller than the set threshold, the initial particle size is the particle size of the micro/nano-sized particles 106.

If the ratio of the approximate spherical radius of the micro/nano-sized particles 106 to the radius of the micropores 103 is greater than the preset threshold, the initial particle size needs to be corrected by a correction coefficient to obtain the particle size of the micro/nano-sized particles 106. The calculation formula is as follows:

$$VR' = (4\rho d^3)S/(\pi D^4)$$

Wherein, the correction coefficient S is determined according to the ratio of the approximate spherical radius of the micro/nano-sized particles 106 to the radius of the micropores 103. For example, the correction coefficient S can be determined according to Table 1.

TABLE 1

| d/D | S |
|---|---|
| 0.1 | 1.00 |
| 0.2 | 1.00 |
| 0.3 | 1.02 |
| 0.4 | 1.05 |
| 0.5 | 1.11 |
| 0.6 | 1.21 |
| 0.7 | 1.38 |
| 0.8 | 1.71 |
| 0.9 | 2.56 |
| 0.95 | 3.86 |

To sum up, according to the device and method provided in this application, three-dimensional morphological attributes such as electric mobility, sphericity value, particle size, of micro/nano-sized particles can be measured, thereby solving the problem that the micro/nano-sized particles in solution state cannot be measured in the existing technology.

The above contents are only preferred exemplary embodiments of the present application, and are not intended to limit the embodiments of the present application. Those of ordinary skill in the art can easily make corresponding changes or modifications according to the main concept and spirit of the present application, therefore, the protection scope of this application shall be subject to the protection scope required by the claims.

What is claimed is:

1. A method for measuring micro/nano-sized particles, the method is applied to a device for measuring micro/nano-sized particles, wherein the device comprises a cavity and at least two microporous membranes, wherein the microporous membranes are arranged in series in the cavity and divide the cavity into a plurality of chambers, wherein each of the microporous membranes is provided with micropores, and two adjacent chambers are in communication via the micropores, and wherein each of the chambers is provided with an electrode, and the method allows the micro/nano-sized particles to be measured to continuously pass through micropores of the device with an electrolyte solution, the method comprising:
    acquiring electrical signal data between two electrodes adjacent to each of the micropores in the process of the micro/nano-sized particles passing through each of the micropores;
    determining attribute data of the micro/nano-sized particles according to the electrical signal data;
    wherein determining attributes data of the micro/nano-sized particles according to the electrical signal data comprising:
    dividing the electrical signal data into a plurality of signal units;
    comparing each the signal unit with the corresponding signal unit of a standard signal respectively, to obtain a contrast coefficient between the electrical signal data and the standard signal;
    acquiring the sphericity value corresponding to the standard signal with the highest contrast coefficient as the sphericity value of the micro/nano-sized particles.

2. The method according to claim 1, wherein the method further comprising:
    calculating an initial particle size of the micro/nano-sized particles according to an electrical conductivity of the electrolyte solution, an approximate spherical radius of a micro/nano-sized particles and the radius of the micropores;

determining a correction coefficient according to the ratio of the approximate spherical radius of the micro/nano-sized particles to the radius of the micro-pore and correcting the initial particle size based on the correction coefficient to obtain a particle size of the micro/nano-sized particles, if the ratio is greater than a preset threshold.

3. The method according to claim 1, wherein the device further comprises a liquid driver located adjacent to the chamber at one end of the cavity for driving the flow of the liquid in the device.

4. The method according to claim 1, wherein in the measurement state, the electrode located at one end of the cavity is grounded, and the remaining electrodes are loaded with voltages of different magnitudes, and the magnitudes of the voltages are ordered corresponding to the distance between the electrode and the ground electrode.

5. The method according to claim 1, wherein in a measurement state, each of the chambers is filled with an electrolyte solution, and the micro/nano-sized particles to be measured pass through the micropores continuously with the electrolyte solution.

6. The method according to claim 1, wherein the shape of the micropores on each of the microporous membranes is the same, and the centers of the micropores are located on the same straight line.

7. A method for measuring micro/nano-sized particles, the method is applied to a device for measuring micro/nano-sized particles, wherein the device comprises a cavity and at least two microporous membranes, wherein the microporous membranes are arranged in series in the cavity and divide the cavity into a plurality of chambers, wherein each of the microporous membranes is provided with micropores, and two adjacent chambers are in communication via the micropores, and wherein each of the chambers is provided with an electrode, and the method allows the micro/nano-sized particles to be measured to continuously pass through micropores of the device with an electrolyte solution, the method comprising:

acquiring electrical signal data between two electrodes adjacent to each of the micropores in the process of the micro/nano-sized particles passing through each of the micropores;

determining attribute data of the micro/nano-sized particles according to the electrical signal data;

wherein determining attributes data of the micro/nano-sized particles according to the electrical signal data comprising:

inputting the electrical signal data into a machine learning model, wherein the machine learning model is obtained by training based on electrical signal data between two adjacent electrodes when a micro/nano-sized object with an asymmetric shape passes through the micropores;

acquiring the three-dimensional shape of the micro/nano-sized particles predicted by the machine learning model based on the electrical signal data.

* * * * *